United States Patent
Negrotto et al.

(10) Patent No.: US 7,521,550 B2
(45) Date of Patent: Apr. 21, 2009

(54) INSECT RESISTANT COTTON PLANTS AND METHODS OF DETECTING THE SAME

(75) Inventors: David Vincent Negrotto, Research Triangle Park, NC (US); Frank Arthur Shotkoski, Ithaca, NY (US); Wenjin Yu, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 28 days.

(21) Appl. No.: 10/580,596

(22) PCT Filed: Nov. 9, 2004

(86) PCT No.: PCT/EP2004/012662

§ 371 (c)(1),
(2), (4) Date: May 25, 2006

(87) PCT Pub. No.: WO2005/054479

PCT Pub. Date: Jun. 16, 2005

(65) Prior Publication Data

US 2007/0067868 A1      Mar. 22, 2007

Related U.S. Application Data

(60) Provisional application No. 60/526,112, filed on Dec. 1, 2003.

(51) Int. Cl.
*C12N 15/32* (2006.01)
(52) U.S. Cl. .................................................. 536/23.71
(58) Field of Classification Search .................. None
See application file for complete search history.

(56) References Cited

FOREIGN PATENT DOCUMENTS

| | | |
|---|---|---|
| EP | 0142924 | 9/1984 |
| WO | 96/10083 | 4/1996 |
| WO | 98/44137 | 10/1998 |
| WO | 02/078437 | 10/2002 |
| WO | 03/013224 | 2/2003 |
| WO | 03/075655 | 9/2003 |
| WO | 2004/039986 | 5/2004 |

OTHER PUBLICATIONS

Barth, Holger et al., The uptake machinery of clostridial actin ADP-ribosylating toxins-a cell delivery for fusion proteins and polypeptides drugs, Naunyn-Schmiedeberg's Arch Pharmacol (2002) 366: 501-512.
Liao. et al., Toxicity of *Bacillus thuringiensis* insecticidal proteins for Helicoverpa armigera and Helicoverpa puncligera (Lepidoptera: Noctuidae), major pests of cotton, Journal of Invertebrate Pathology 80 (2202) 55-63.
Rothstein, Steven J., et al., Promotor cassettes, anti-biotic-resistance genes, and vectors for plant transformation. Gene (1987) 53: 153-161.
Umbeck, P., et al., Genetically transformed cotton (*Gossypium hirsutum* L.) plants. Biotechnoology (1987) 5:263-266.
Rajguru, S. N., et al., Assessment of resistance of cotton transformed with lectin genes to tobacco budworm (Heliothis virescens). Proceedings of the Beltwide Cotton Conference (1998) 1:490-491.
Database EMBL [Online] "Mus musculus clone RP23-182G17, Low_Pass Sequence Sampling", XP002318755 retrieved from EBI accession No. EM_PRO:AC101211 Positions 51663-51683, Nov. 25, 2001.
Database EMBL [Online] "Mus musculus BAC clone RP23-307E9-from chromosome 7, complete sequence." XP002318982 retrieved from EBI accession No. EM_PRO:AC131669 Positions 14695-14715, Aug. 28, 2002.
Anonymous: "Application for license for dealings involving an intentional release into the environment DIR 036/2003, Title: Breeding and pre-commercial evaluation of transgenic cotton expressing a vegetative insecticidal protein (VIP) and a herbicide tolerance gene", Internet Article, [Online] Oct. 2003, XP002318972 Australia. Retrieved from the Internet: URL:http//www.ogtr.gov.au/pdf/ir/dir036finalrarmp.pdf> 'retrieved on Feb. 22, 2005.
Rice, "Specific Primers for the Detection fo Vip3A insecticidal gene within a *Bacillus thuringiensis* collection" Letters in Applied Microbiology, vol. 28, No. 5, May 1999 pp. 378-382, XP002318971.
Selvapandiyan et al., "Toxicity analysis of N-and C- terminus-deleted vegetative insecticidal protein from *Bacillus thuringiensis*" Applied and Environmental Microbiology. Washington, DC, US vol. 67, No. 12, Dec. 2002 pp. 5855-5858, XP002251845.
Yu et al., "The *Bacillus thuringiensis* Vegetative Insecticidal Protein VIP3A Lyses Midgut Epithelim Cells of Susceptible Insects", Applied and Environmental Microbiology, Washington, DC, vol. 63, No. 2, Feb. 1997 pp. 532-536, XP000673006.

*Primary Examiner*—Anne R Kubelik
(74) *Attorney, Agent, or Firm*—Gregory W. Warren

(57) ABSTRACT

The present application relates to an insect resistant transgenic cotton event designated COT202. The application also relates to polynucleotides which are characteristic of the COT202 event, plants comprising the polynucleotides, and methods of detecting the COT202 event.

2 Claims, No Drawings

SEQUENCE LISTING

<160> NUMBER OF SEQ ID NOS: 18

<210> SEQ ID NO 1
<211> LENGTH: 26
<212> TYPE: DNA
<213> ORGANISM: Artificial Sequence
<220> FEATURE:
<223> OTHER INFORMATION: COT202 nucleotide motif

<400> SEQUENCE: 1
aacaaacaca aaatcttttc accagt                                          26

<210> SEQ ID NO 2
<211> LENGTH: 26
<212> TYPE: DNA
<213> ORGANISM: Artificial Sequence
<220> FEATURE:
<223> OTHER INFORMATION: COT202 nucleotide motif

<400> SEQUENCE: 2
ttcccgcctt cagattttct gcaaca                                          26

<210> SEQ ID NO 3
<211> LENGTH: 23
<212> TYPE: DNA
<213> ORGANISM: Artificial Sequence
<220> FEATURE:
<223> OTHER INFORMATION: COT202 nucleotide motif

<400> SEQUENCE: 3
ggtgtccatc gggtagtcca taa                                             23

<210> SEQ ID NO 4
<211> LENGTH: 24
<212> TYPE: DNA
<213> ORGANISM: Artificial Sequence
<220> FEATURE:
<223> OTHER INFORMATION: COT202 nucleotide motif

<400> SEQUENCE: 4
tctatgttac tagatcggga attg                                            24

<210> SEQ ID NO 5
<211> LENGTH: 20
<212> TYPE: DNA
<213> ORGANISM: Artificial Sequence
<220> FEATURE:
<223> OTHER INFORMATION: COT202 nucleotide motif

<400> SEQUENCE: 5
gatcggggtc aggaaggtct                                                 20

<210> SEQ ID NO 6
<211> LENGTH: 20
<212> TYPE: DNA
<213> ORGANISM: Artificial Sequence
<220> FEATURE:
<223> OTHER INFORMATION: COT202 nucleotide motif

<400> SEQUENCE: 6
cagcatcatg aacgagcact                                                 20

<210> SEQ ID NO 7
<211> LENGTH: 290

<212> TYPE: DNA
<213> ORGANISM: Artificial Sequence
<220> FEATURE:
<223> OTHER INFORMATION: COT202 nucleotide motif

<400> SEQUENCE: 7

| | | | | | |
|---|---|---|---|---|---|
| gacaaggaca | gcttgagcga | ggtgatctac | ggcgacatgg | acaagctgct | gtgtccggac | 60 |
| cagagcgagc | aaatctacta | caccaacaac | atcgtgttcc | cgaacgagta | cgtgatcacc | 120 |
| aagatcgact | tcaccaagaa | gatgaagacc | ctgcgctacg | aggtgaccgc | caacttctac | 180 |
| gacagcagca | ccggcgagat | cgacctgaac | aagaagaagg | tggagagcag | cgaggccgag | 240 |
| taccgcaccc | tgagcgcgaa | cgacgacggc | gtctacatgc | cactgggcgt | | 290 |

<210> SEQ ID NO 8
<211> LENGTH: 4382
<212> TYPE: DNA
<213> ORGANISM: Artificial Sequence
<220> FEATURE:
<223> OTHER INFORMATION: COT202 nucleotide motif

<400> SEQUENCE: 8

| | | | | | |
|---|---|---|---|---|---|
| gatttggagc | caagtctcat | aaacgccatt | gtggaagaaa | gtcttgagtt | ggtggtaatg | 60 |
| taacagagta | gtaagaacag | agaagagaga | gagtgtgaga | tacatgaatt | gtcgggcaac | 120 |
| aaaaatcctg | aacatcttat | tttagcaaag | agaaagagtt | ccgagtctgt | agcagaagag | 180 |
| tgaggagaaa | tttaagctct | tggacttgtg | aattgttccg | cctcttgaat | acttcttcaa | 240 |
| tcctcatata | ttcttcttct | atgttacctg | aaaaccggca | tttaatctcg | cgggtttatt | 300 |
| ccggttcaac | attttttttg | ttttgagtta | ttatctgggc | ttaataacgc | aggcctgaaa | 360 |
| taaattcaag | gcccaactgt | tttttttttt | aagaagttgc | tgttaaaaaa | aaaaaaaggg | 420 |
| aattaacaac | aacaacaaaa | aaagataaag | aaaataataa | caattacttt | aattgtagac | 480 |
| taaaaaaaca | tagattttat | catgaaaaaa | agagaaaaga | aataaaaact | tggatcaaaa | 540 |
| aaaaacatac | agatcttcta | attattaact | tttcttaaaa | attaggtcct | ttttcccaac | 600 |
| aattaggttt | agagttttgg | aattaaacca | aaaagattgt | tctaaaaaat | actcaaattt | 660 |
| ggtagataag | tttccttatt | ttaattagtc | aatggtagat | acttttttttt | cttttctttta | 720 |
| ttagagtaga | ttagaatctt | ttatgccaag | tattgataaa | ttaaatcaag | aagataaact | 780 |
| atcataatca | acatgaaatt | aaaagaaaaa | tctcatatat | agtattagta | ttctctatat | 840 |
| atattatgat | tgcttattct | taatgggttg | ggttaaccaa | gacatagtct | taatggaaag | 900 |
| aatctttttt | gaacttttttc | cttattgatt | aaattcttct | atagaaaaga | aagaaattat | 960 |
| ttgaggaaaa | gtatatacaa | aaagaaaaat | agaaaaatgt | cagtgaagca | gatgtaatgg | 1020 |
| atgacctaat | ccaaccacca | ccataggatg | tttctacttg | agtcggtctt | ttaaaaacgc | 1080 |
| acggtggaaa | atatgacacg | tatcatatga | ttccttcctt | tagtttcgtg | ataataatcc | 1140 |
| tcaactgata | tcttcctttt | tttgttttgg | ctaaagatat | tttattctca | ttaatagaaa | 1200 |
| agacggtttt | gggcttttgg | tttgcgatat | aaagaagacc | ttcgtgtgga | agataataat | 1260 |
| tcatcctttc | gtctttttct | gactcttcaa | tctctcccaa | agcctaaagc | gatctctgca | 1320 |
| aatctctcgc | gactctctct | ttcaaggtat | attttctgat | tcttttttgtt | tttgattcgt | 1380 |
| atctgatctc | caattttttgt | tatgtggatt | attgaatctt | ttgtataaat | tgcttttgac | 1440 |
| aatattgttc | gtttcgtcaa | tccagcttct | aaatttttgtc | ctgattacta | agatatcgat | 1500 |
| tcgtagtgtt | tacatctgtg | taatttcttg | cttgattgtg | aaattaggat | tttcaaggac | 1560 |

-continued

```
gatctattca attttttgtgt tttctttgtt cgattctctc tgttttaggt ttcttatgtt    1620
tagatccgtt tctctttggt gttgttttga tttctcttac ggcttttgat ttggtatatg    1680
ttcgctgatt ggtttctact tgttctattg tttttatttca ggtggatcca ccatgaacaa    1740
gaacaacacc aagctgagca cccgcgccct gccgagcttc atcgactact tcaacggcat    1800
ctacggcttc gccaccggca tcaaggacat catgaacatg atcttcaaga ccgacaccgg    1860
cggcgacctg accctggacg agatcctgaa gaaccagcag ctgctgaacg acatcagcgg    1920
caagctggac ggcgtgaacg gcagcctgaa cgacctgatc gcccagggca acctgaacac    1980
cgagctgagc aaggagatcc ttaagatcgc caacgagcag aaccaggtgc tgaacgacgt    2040
gaacaacaag ctggacgcca tcaacaccat gctgcgcgtg tacctgccga agatcaccag    2100
catgctgagc gacgtgatga agcagaacta cgccctgagc ctgcagatcg agtacctgag    2160
caagcagctg caggagatca gcgacaagct ggacatcatc aacgtgaacg tcctgatcaa    2220
cagcaccctg accgagatca ccccggccta ccagcgcatc aagtacgtga acgagaagtt    2280
cgaagagctg accttcgcca ccgagaccag cagcaaggtg aagaaggacg gcagcccggc    2340
cgacatcctg gacgagctga ccgagctgac cgagctggcg aagagcgtga ccaagaacga    2400
cgtggacggc ttcgagttct acctgaacac cttccacgac gtgatggtgg gcaacaacct    2460
gttcggccgc agcgccctga agaccgccag cgagctgatc accaaggaga acgtgaagac    2520
cagcggcagc gaggtgggca cgtgtacaa cttcctgatc gtgctgaccg ccctgcaggc    2580
ccaggccttc ctgacccctga ccacctgtcg caagctgctg ggcctggccg acatcgacta    2640
caccagcatc atgaacgagc acttgaacaa ggagaaggag gagttccgcg tgaacatcct    2700
gccgaccctg agcaacacct tcagcaaccc gaactacgcc aaggtgaagg gcagcgacga    2760
ggacgccaag atgatcgtgg aggctaagcc gggccacgcg ttgatcggct tcgagatcag    2820
caacgacagc atcaccgtgc tgaaggtgta cgaggccaag ctgaagcaga actaccaggt    2880
ggacaaggac agcttgagcg aggtgatcta cggcgacatg gacaagctgc tgtgtccgga    2940
ccagagcgag caaatctact acaccaacaa catcgtgttc ccgaacgagt acgtgatcac    3000
caagatcgac ttcaccaaga agatgaagac cctgcgctac gaggtgaccg ccaacttcta    3060
cgacagcagc accggcgaga tcgacctgaa caagaagaag gtggagagca gcgaggccga    3120
gtaccgcacc ctgagcgcga acgacgacgg cgtctacatg ccactgggcg tgatcagcga    3180
gaccttcctg accccgatca acggctttgg cctgcaggcc gacgagaaca gccgcctgat    3240
caccctgacc tgtaagagct acctgcgcga gctgctgcta gccaccgacc tgagcaacaa    3300
ggagaccaag ctgatcgtgc caccgagcgg cttcatcagc aacatcgtgg agaacggcag    3360
catcgaggag gacaacctgg agccgtggaa ggccaacaac aagaacgcct acgtggacca    3420
caccggcggc gtgaacggca ccaaggccct gtacgtgcac aaggacggcg gcatcagcca    3480
gttcatcggc gacaagctga agccgaagac cgagtacgtg atccagtaca ccgtgaaggg    3540
caagccatcg attcacctga aggacgagaa caccggctac atccactacg aggacaccaa    3600
caacaacctg gaggactacc agaccatcaa caagcgcttc accaccggca ccgacctgaa    3660
gggcgtgtac ctgatcctga agagccagaa cggcgacgag gcctggggcg acaacttcat    3720
catcctggag atcagcccga gcgagaagct gctgagcccg gagctgatca acaccaacaa    3780
ctggaccagc accggcagca ccaacatcag cggcaacacc ctgacccctgt accagggcgg    3840 ccgcggcatc ctgaagcaga acctgcagct ggacagcttc agcacctacc gcgtgtactt    3900
cagcgtgagc ggcgacgcca acgtgcgcat ccgcaactcc cgcgaggtgc tgttcgagaa    3960
```

```
gaggtacatg agcggcgcca aggacgtgag cgagatgttc accaccaagt tcgagaagga    4020
caacttctac atcgagctga gccagggcaa caacctgtac ggcggcccga tcgtgcactt    4080
ctacgacgtg agcatcaagt aggagctcta gatccccgga atttcccga tcgttcaaac     4140 atttggcaat aaagtttctt aagattgaat cctgttgccg gtcttgcgat gattatcata    4200
taatttctgt tgaattacgt taagcatgta ataattaaca tgtaatgcat gacgttattt    4260
atgagatggg tttttatgat tagagtcccg caattataca tttaatacgc gatagaaaac    4320
aaaatatagc gcgcaaacta ggataaatta tcgcgcgcgg tgtcatctat gttactagat    4380
cg                                                                  4382
```

<210> SEQ ID NO 9
<211> LENGTH: 789
<212> TYPE: PRT
<213> ORGANISM: Artificial Sequence
<220> FEATURE:
<223> OTHER INFORMATION: VIP3A protein motif

<400> SEQUENCE: 9

```
Met Asn Lys Asn Asn Thr Lys Leu Ser Thr Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Asp Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Arg Val Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Ser Ser Lys Val Lys Lys Asp Gly Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Thr Lys Glu Asn Val Lys Thr Ser Gly Ser Glu Val Gly Asn Val Tyr
            260                 265                 270

Asn Phe Leu Ile Val Leu Thr Ala Leu Gln Ala Gln Ala Phe Leu Thr
```

-continued

```
                275                 280                 285
Leu Thr Thr Cys Arg Lys Leu Leu Gly Leu Ala Asp Ile Asp Tyr Thr
290                 295                 300
Ser Ile Met Asn Glu His Leu Asn Lys Glu Lys Glu Glu Phe Arg Val
305                 310                 315                 320
Asn Ile Leu Pro Thr Leu Ser Asn Thr Phe Ser Asn Pro Asn Tyr Ala
                325                 330                 335
Lys Val Lys Gly Ser Asp Glu Asp Ala Lys Met Ile Val Glu Ala Lys
                340                 345                 350
Pro Gly His Ala Leu Ile Gly Phe Glu Ile Ser Asn Asp Ser Ile Thr
                355                 360                 365
Val Leu Lys Val Tyr Glu Ala Lys Leu Lys Gln Asn Tyr Gln Val Asp
370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                405                 410                 415
Pro Asn Glu Tyr Val Ile Thr Lys Ile Asp Phe Thr Lys Lys Met Lys
                420                 425                 430
Thr Leu Arg Tyr Glu Val Thr Ala Asn Phe Tyr Asp Ser Ser Thr Gly
                435                 440                 445
Glu Ile Asp Leu Asn Lys Lys Lys Val Glu Ser Ser Glu Ala Glu Tyr
                450                 455                 460
Arg Thr Leu Ser Ala Asn Asp Asp Gly Val Tyr Met Pro Leu Gly Val
465                 470                 475                 480
Ile Ser Glu Thr Phe Leu Thr Pro Ile Asn Gly Phe Gly Leu Gln Ala
                485                 490                 495
Asp Glu Asn Ser Arg Leu Ile Thr Leu Thr Cys Lys Ser Tyr Leu Arg
                500                 505                 510
Glu Leu Leu Leu Ala Thr Asp Leu Ser Asn Lys Glu Thr Lys Leu Ile
                515                 520                 525
Val Pro Pro Ser Gly Phe Ile Ser Asn Ile Val Glu Asn Gly Ser Ile
530                 535                 540
Glu Glu Asp Asn Leu Glu Pro Trp Lys Ala Asn Asn Lys Asn Ala Tyr
545                 550                 555                 560
Val Asp His Thr Gly Gly Val Asn Gly Thr Lys Ala Leu Tyr Val His
                565                 570                 575
Lys Asp Gly Gly Ile Ser Gln Phe Ile Gly Asp Lys Leu Lys Pro Lys
                580                 585                 590
Thr Glu Tyr Val Ile Gln Tyr Thr Val Lys Gly Lys Pro Ser Ile His
                595                 600                 605
Leu Lys Asp Glu Asn Thr Gly Tyr Ile His Tyr Glu Asp Thr Asn Asn
                610                 615                 620
Asn Leu Glu Asp Tyr Gln Thr Ile Asn Lys Arg Phe Thr Thr Gly Thr
625                 630                 635                 640
Asp Leu Lys Gly Val Tyr Leu Ile Leu Lys Ser Gln Asn Gly Asp Glu
                645                 650                 655
Ala Trp Gly Asp Asn Phe Ile Ile Leu Glu Ile Ser Pro Ser Glu Lys
                660                 665                 670
Leu Leu Ser Pro Glu Leu Ile Asn Thr Asn Asn Trp Thr Ser Thr Gly
                675                 680                 685
Ser Thr Asn Ile Ser Gly Asn Thr Leu Thr Leu Tyr Gln Gly Gly Arg
                690                 695                 700
```

-continued

Gly Ile Leu Lys Gln Asn Leu Gln Leu Asp Ser Phe Ser Thr Tyr Arg
705                 710                 715                 720

Val Tyr Phe Ser Val Ser Gly Asp Ala Asn Val Arg Ile Arg Asn Ser
            725                 730                 735

Arg Glu Val Leu Phe Glu Lys Arg Tyr Met Ser Gly Ala Lys Asp Val
        740                 745                 750

Ser Glu Met Phe Thr Thr Lys Phe Glu Lys Asp Asn Phe Tyr Ile Glu
    755                 760                 765

Leu Ser Gln Gly Asn Asn Leu Tyr Gly Gly Pro Ile Val His Phe Tyr
770                 775                 780

Asp Val Ser Ile Lys
785

<210> SEQ ID NO 10
<211> LENGTH: 20
<212> TYPE: DNA
<213> ORGANISM: Artificial Sequence
<220> FEATURE:
<223> OTHER INFORMATION: COT202 nucleotide motif

<400> SEQUENCE: 10
ggtccctgga tacggtgtca                                          20

<210> SEQ ID NO 11
<211> LENGTH: 20
<212> TYPE: DNA
<213> ORGANISM: Artificial Sequence
<220> FEATURE:
<223> OTHER INFORMATION: COT202 nucleotide motif

<400> SEQUENCE: 11
ttgagggttg gatcctttgc                                          20

<210> SEQ ID NO 12
<211> LENGTH: 26
<212> TYPE: DNA
<213> ORGANISM: Artificial Sequence
<220> FEATURE:
<223> OTHER INFORMATION: COT202 nucleotide motif
<220> FEATURE:
<221> NAME/KEY: modified_base
<222> LOCATION: (1)..(1)
<223> OTHER INFORMATION: VIC label at 5' end
<220> FEATURE:
<221> NAME/KEY: modified_base
<222> LOCATION: (26)..(26)
<223> OTHER INFORMATION: TAMRA label at 3' end

<400> SEQUENCE: 12
caccaacatc atcaatggtg gcatcg                                   26

<210> SEQ ID NO 13
<211> LENGTH: 20
<212> TYPE: DNA
<213> ORGANISM: Artificial Sequence
<220> FEATURE:
<223> OTHER INFORMATION: COT202 nucleotide motif

<400> SEQUENCE: 13
ggaatgtggc gaatggtgat                                          20

<210> SEQ ID NO 14
<211> LENGTH: 18
<212> TYPE: DNA

```
<213> ORGANISM: Artificial Sequence
<220> FEATURE:
<223> OTHER INFORMATION: COT202 nucleotide motif

<400> SEQUENCE: 14
tgtcgtttcc cgccttca                                                      18

<210> SEQ ID NO 15
<211> LENGTH: 29
<212> TYPE: DNA
<213> ORGANISM: Artificial Sequence
<220> FEATURE:
<223> OTHER INFORMATION: COT202 nucleotide motif
<220> FEATURE:
<221> NAME/KEY: modified_base
<222> LOCATION: (1)..(1)
<223> OTHER INFORMATION: FAM label at 5' end
<220> FEATURE:
<221> NAME/KEY: modified_base
<222> LOCATION: (29)..(29)
<223> OTHER INFORMATION: TAMRA label at 3' end

<400> SEQUENCE: 15
caaattgccc atttcattca tccaaaagc                                          29

<210> SEQ ID NO 16
<211> LENGTH: 23
<212> TYPE: DNA
<213> ORGANISM: Artificial Sequence
<220> FEATURE:
<223> OTHER INFORMATION: COT202 nucleotide motif

<400> SEQUENCE: 16
ggtgtccatc gggtagtcca taa                                                23

<210> SEQ ID NO 17
<211> LENGTH: 24
<212> TYPE: DNA
<213> ORGANISM: Artificial Sequence
<220> FEATURE:
<223> OTHER INFORMATION: COT202 nucleotide motif

<400> SEQUENCE: 17
tgagtaggag atgtaagttg gcgc                                               24

<210> SEQ ID NO 18
<211> LENGTH: 24
<212> TYPE: DNA
<213> ORGANISM: Artificial Sequence
<220> FEATURE:
<223> OTHER INFORMATION: COT202 nucleotide motif

<400> SEQUENCE: 18
tctatgttac tagatcggga attg                                               24
```

INSECT RESISTANT COTTON PLANTS AND METHODS OF DETECTING THE SAME

This is a §371 of PCT/EP2004/012662, filed Nov. 9, 2004, and published Jun. 16, 2005, as WO 05/054479, which claims priority to U.S. Provisional Application No. 60/526,112, filed Dec. 1, 2003, which is hereby incorporated by reference in its entirety.

The present invention relates to genetic engineering of plants and in particular to an insect resistant transgenic cotton plant. Specifically, the invention relates to a cotton plant designated COT202 which comprises a VIP3A gene. It also relates to methods of detecting material derived from the plant.

Plant pests are a major factor in the loss of the world's important agricultural crops. About $8 billion is lost every year in the U.S. due to infestations of plants by non-mammalian pests including insects. In addition to losses in field crops, insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Good control of insect pests can thus be reached, but these chemicals can sometimes also affect other, beneficial insects. Another problem resulting from the wide use of chemical pesticides is the appearance of resistant insect varieties. This has been partially alleviated by various resistance management practices, but there is an increasing need for alternative pest control agents. Biological pest control agents, such as *Bacillus thuringiensis* strains expressing pesticidal toxins like δ-endotoxins, have also been applied to crop plants with satisfactory results, offering an alternative or compliment to chemical pesticides. The genes coding for some of these δ-endotoxins have been isolated and their expression in heterologous hosts has been shown to provide another tool for the control of economically important insect pests. In particular, the expression of insecticidal toxins such as *Bacillus thuringiensis* δ-endotoxins in transgenic plants, has provided efficient protection against selected insect pests, and transgenic plants expressing such toxins have been commercialized, allowing farmers to reduce applications of chemical insect control agents.

Recently, a new family of insecticidal proteins produced by *Bacillus* sp. during the vegetative stages of growth (vegetative insecticidal proteins (VIPs)) has been identified.

U.S. Pat. Nos. 5,877,012, 6,107,279, and 6,137,033 describe vip3A toxin genes isolated from *Bacillus* species. The VIP3A toxins possess insecticidal activity against a wide spectrum of lepidopteran insects including but not limited to fall armyworm, *Spodoptera frugiperda*, black cutworm, *Agrotis ipsilon*, sugarcane borer, *Diatraea saccharalis*, and lesser cornstalk borer, *Elasmopalpus lignosellus*, and when expressed in transgenic plants, for example cotton, confer protection on the plant from insect feeding damage.

The cotton family, genus *Gossypium*, a member of the Malvaceae, consists of 39 species, of which *Gossypium hirsutum* is the most commonly cultivated species. Three other species are also cultivated: *G. arboreum, G. barbadense*, and *G. herbaceum*. These cultivated species are grown primarily for the seed hairs that are made into textiles. Cotton is suitable as a textile fibre because the mature dry hairs twist in such a way that fine strong threads can be spun from them. Other products, such as cottonseed oil, cake, and cotton linters are by-products of fibre production.

Damage to cotton crops by insect pests throughout the world results in a significant yield loss each year. Effective control of these pests to minimize yield loss is of great economic importance. Examples of insect pests of cotton include Beet armyworm (*Spodoptera exigua*), Boll weevil (*Anthonomus grandis grandis*), Cabbage looper (*Trichoplusia ni*), Clouded plant bug (*Neurocolpus nubilus*), Cotton aphid (*Aphis gossypii*), Cotton bollworm (*Heliocoverpa zea*), Cutworms (*Feltia subterranea, Peridroma saucia, Agrotis ipsilon*), European corn borer (*Ostrinia nubilalis*), Fall armyworm (*Spodoptera fugiperda*), Seedling thrips (*Frankliniella* spp.), Soybean looper (*Pseudoplusia includens*), Stink bugs (*Nezara viridula, Acrosternum hilare, Euschistus servus*), Tarnished plant bug (*Lygus lineolaris*), Tobacco budworm (*Heliothis virescens*) and Whiteflies (*Trialeurodes abutilonea, Bemisia tabaci*).

Transformation and regeneration of cotton plants is now a well-established procedure, typically based on *Agrobacterium tumefaciens* mediated transfer of foreign DNA into cotton plant parts and regeneration of said plant parts in tissue culture into fully fertile, transgenic cotton plants.

There exists a requirement to generate a cotton plant that is insect resistant so that yield loss through damage to cotton crops by insect pests is reduced. An insect resistant cotton plant could reduce the need to apply chemical pesticides, which may be detrimental to other, beneficial insects and the environment. Further, it is desirable to provide an insect resistant plant that comprises a VIP gene, as an alternative to transgenic plants comprising crystal proteins from *Bacillus thuringiensis*. This may be of use in insect resistance management.

Therefore, the present invention relates to an insect resistant transgenic cotton event, designated COT202. It also relates to methods of detecting plant material derived therefrom. "COT202 event" in the context of this application refers to the original insecticidal transgenic cotton plant described herein. "Insecticidal" as used herein refers to any inhibitory effect on an insect, including but not limited to reduced feeding, retarded growth, reduced fecundity, paralysis or death. "Fecundity" comprises all aspects related to reproduction such as reproductive ability, reproductive frequency and number of offspring. Also embraced by this invention is any plant material derived from the COT202 event, including seeds.

The COT202 event exhibits a novel genotype comprising at least one expression cassette. The cassette comprises a suitable promoter for expression in plants operably linked to a gene that encodes a VIP3A insecticidal toxin, useful in controlling a wide spectrum of lepidopteran insect pests, and a suitable polyadenylation signal. Suitable promoters may be isolated from, inter alia, plants. Numerous plant promoters have been isolated and characterised including constitutive, switchable and/or tissue specific promoters. Suitable promoters may be selected from the following, non-limiting group: CaMV35S, FMV35S, Ubiquitin, Act2, NOS, OCS, Cestrum yellow leaf curl virus promoter, Patatin, E9, alcA/alcR switch, GST switch, RMS switch, oleosin, Gelvin, ribulose bisphosphate carboxylase-oxygenase small sub-unit, actin 7, MR7 promoter (maize), Gos 9 (rice), GOS2 promoters, Mas-Ocs (or super promoter), RolD promoter (*Agrobacterium rhizogenes*), SuperMAS promoter, and Suc2 promoter (*Arabidopsis*). In one embodiment of the present invention, the promoter is the Ubiquitin promoter, UBQ3, from *Arabidopsis thaliana*. Additional elements such as enhancer sequences may also be incorporated into the expression cassette in order to boost levels of gene expression, for example transcriptional or translational enhancers such as tobacco etch virus (TEV) translation activator CaMV35S enhancer, and FMV35S enhancer. Alternatively it may be desirable to include a targeting sequence, for example, to direct transportation of the VIP3A toxin to a particular cellular compartment. For example if it is desired to provide the protein outside of the cell then an extracellular targeting sequence may be ligated to the polynucleotide encoding the VIP protein. Other examples of targeting include targeting to a specific intracellular organelle or compartment, for example to the endoplasmic reticulum using the retention sequence described in Munro, S. and Pelham, H. R. A C-terminal signal prevents secretion of luminal ER proteins. Cell 48(5): 899-907 (1987). Numerous polyadenylation signals have been isolated and characterised. Examples of suitable polyadenylation signals functional in plants include that from the nopaline synthase gene (nos) of *Agrobacterium tumefaciens*, from the proteinase inhibitor II gene and from the alpha-tubulin gene (EP-A 652, 286). In one embodiment of the present invention, the polyadenylation signal is that from the nos gene of *Agrobacterium tumefaciens*.

According to the invention, the polynucleotide encoding the VIP3A protein may also be codon-optimised or otherwise altered to enhance for example, transcription once it is incorporated into plant material. Such codon optimisation may also be used to alter the predicted secondary structure of the RNA transcript produced in any transformed cell, or to destroy cryptic RNA instability elements present in the unaltered transcript, thereby increasing the stability and/or availability of the transcript in the transformed cell (Abler and Green (1996) Plant Molecular Biology (32) pp. 63-78).

In a precursor to the COT202 event, a second cassette is present that comprises a gene which, when expressed, can be used as a selectable marker. Numerous selectable markers have been characterised, including some that confer tolerance to antibiotics and others that confer tolerance to herbicides. Examples of suitable selectable marker genes include those that confer tolerance to hygromycin, kanamycin or gentamycin. Further suitable selectable markers include genes that confer resistance to herbicides such as glyphosate-based herbicides or resistance to toxins such as eutypine. Other forms of selection are also available such as hormone based selection systems such as the Multi Auto Transformation (MAT) system of Hiroyrasu Ebinuma et al. (1997) PNAS Vol. 94 pp. 2117-2121; visual selection systems which use the known green fluorescence protein, β glucoronidase; and any other selection system such as mannose isomerase (Positech™), xylose isomerase and 2-deoxyglucose (2-DOG). In one embodiment of the present invention, the selectable marker gene is one that confers tolerance to hygromycin. This second expression cassette is useful for selecting transformants during and following plant transformation. Optionally, it may be segregated away from the COT202 event precursor after transformation to leave the COT202 event itself The COT202 event per se does not comprise a selectable marker cassette. Further expression cassettes are optionally comprised in the COT202 event. For example these may provide other desirable benefits such as herbicide resistance.

The expression cassettes may be introduced into the plant on the same or different plasmids. If the expression cassettes are present on the same plasmid and introduced into the plant via an *Agrobacterium*-mediated transformation method, they may be present within the same or different T-DNA regions. In one embodiment of the present invention, two expression cassettes are present on different T-DNA regions within the same plasmid.

According to the first aspect of the invention, there is provided a polynucleotide comprising at least 17 contiguous nucleotides from the 26-nucleotide sequence of SEQ ID NO: 1. In one embodiment said polynucleotide comprises at least 18 contiguous nucleotides from SEQ ID NO: 1. In a further embodiment said polynucleotide comprises at least 20 contiguous nucleotides from SEQ ID NO: 1. In a still further embodiment said polynucleotide comprises at least 22 contiguous nucleotides from SEQ ID NO: 1. In a further embodiment said polynucleotide comprises at least 23 contiguous nucleotides from SEQ ID NO: 1. In yet a further embodiment said polynucleotide comprises at least 24 contiguous nucleotides from SEQ ID NO: 1. In a further embodiment said polynucleotide comprises at least 25 contiguous nucleotides from SEQ ID NO: 1. In a still further embodiment there is provided a polynucleotide comprising the sequence of SEQ ID NO: 1.

In a further aspect of the invention, there is provided a polynucleotide comprising at least 17 contiguous nucleotides from the 26-nucleotide sequence of SEQ ID NO: 2. In one embodiment said polynucleotide comprises at least 18 contiguous nucleotides from SEQ ID NO: 2. In a further embodiment said polynucleotide comprises at least 20 contiguous nucleotides from SEQ ID NO: 2. In a still further embodiment said polynucleotide comprises at least 22 contiguous nucleotides from SEQ ID NO: 2. In a further embodiment said polynucleotide comprises at least 23 contiguous nucleotides from SEQ ID NO: 2. In yet a further embodiment said polynucleotide comprises at least 24 contiguous nucleotides from SEQ ID NO: 2. In a further embodiment said polynucleotide comprises at least 25 contiguous nucleotides from SEQ ID NO: 2. In a still further embodiment there is provided a polynucleotide comprising the sequence of SEQ ID NO: 2.

In a further aspect of the present invention there is provided a polynucleotide as described above the comprising the sequence of SEQ ID NO: 7. In a further aspect of the present invention there is provided a polynucleotide as described above further comprising the sequence of SEQ ID NO: 8.

In another aspect of the present invention there is provided a plant comprising a polynucleotide which comprises at least 17 contiguous nucleotides of SEQ ID NO: 1 and/or SEQ ID NO: 2. In one embodiment said plant comprises at least 18 contiguous nucleotides of SEQ ID NO: 1 and/or SEQ ID NO: 2. In a further embodiment said plant comprises at least 20 contiguous nucleotides of SEQ ID NO: 1 and/or SEQ ID NO: 2. In a further embodiment said plant comprises at least 22 contiguous nucleotides of SEQ ID NO: 1 and/or SEQ ID NO: 2. In a further embodiment said plant comprises at least 23 contiguous nucleotides of SEQ ID NO: 1 and/or SEQ ID NO: 2. In a still further embodiment said plant comprises at least 24 contiguous nucleotides of SEQ ID NO: 1 and/or SEQ ID NO: 2. In a further embodiment said plant comprises at least 25 contiguous nucleotides of SEQ ID NO: 1 and/or SEQ ID NO: 2. In yet a further embodiment said plant comprises the sequence of SEQ ID NO: 1 and/or SEQ ID NO: 2. In a further embodiment, said plant additionally comprises the sequence of SEQ ID NO: 7. In a further embodiment still, said plant additionally comprises the sequence of SEQ ID NO: 8. In one embodiment of the present invention, said plant is a cotton plant. In a further embodiment, said plant is an insecticidal cotton plant which is the COT202 event, or a plant derived therefrom.

The skilled man is familiar with plant transformation methods. In particular, two principal techniques have been characterised across a wide range of plant species: transformation by *Agrobacterium* and transformation by direct DNA transfer.

*Agrobacterium*-mediated transformation is a commonly used method for transformation of dicotyledonous plants. The foreign DNA to be introduced into the plant is cloned into a binary vector in between left and right border consensus sequences. This is the T-DNA region. The binary vector is transferred into an *Agrobacterium* cell, which is subsequently used to infect plant tissue. The T-DNA region of the vector comprising the foreign DNA is inserted into the plant genome. The marker gene cassette and trait gene cassette may be present on the same T-DNA region, different T-DNA regions in the same vector, or even different T-DNA regions in different vectors. In one embodiment of the present invention, the cassettes are present on different T-DNA regions in the same vector.

Alternatively, direct DNA transfer can be used to introduce the DNA directly into a plant cell. One suitable method of direct transfer may be bombardment of plant cells with a vector comprising the DNA for insertion using a particle gun (particle-mediated biolistic transformation); another established method, 'whiskers', involves coating the DNA onto silicon carbide fibres onto which cells are impaled. Other methods for transforming plant cells include protoplast transformation (optionally in the presence of polyethylene glycols); sonication of plant tissues, cells or protoplasts in a medium comprising the polynucleotide or vector; micro-insertion of the polynucleotide or vector into plant material (optionally employing the known silicon carbide "whiskers" technique), electroporation and the like.

Following transformation, transgenic plants must be regenerated from the transformed plant tissue, and progeny possessing the foreign DNA selected using an appropriate marker such as resistance to hygromycin. The skilled man is familiar with the composition of suitable regeneration media. The selectable marker can be segregated away from transgenic events by conventional plant breeding methods, thus resulting in, for example, the COT202 event.

A plant of the invention, as described herein, has an insecticidal effect on insects from one or more species from the group comprising *Heliothis* sp., *Helicoverpa* sp. and *Spodoptera* sp. which may infest it. "Infest" as used herein refers to attack, colonisation, feeding or damage in any way by one or more insects. Thus, for example, the plant of the present invention will provide a self-defense mechanism against infestation by pest insects such as *Helicoverpa zea* (cotton boll worm). As a result, a reduced number of insecticide sprays are required during the cultivation of said plant compared to a non-transgenic cotton plant of the same variety and yield loss through insect pests is kept at a minimal level.

The present invention is not limited to the COT202 event itself, but is further extended to include any plant material derived therefrom, including seeds in so far as they contain at least one of the present inventive polynucleotides. The present invention includes, but is not limited to plants that are derived from a breeding cross with the COT202 event or a derivative therefrom by conventional breeding or other methods. The invention also includes plant material derived from the COT202 event that may comprise additional, modified or fewer polynucleotide sequences compared to the COT202 event or exhibit other phenotypic characteristics. For example it may be desirable to transform plant material derived from the COT202 event to generate a new event that possesses an additional trait, such as a second insect resistance gene. This process is known as gene stacking. The second insect resistance gene may encode, for example insecticidal lectins, insecticidal protease inhibitors and insecticidal proteins derived from species of the *Bacillus thuringiensis, Xenorhabdus nematophilus*, or *Photorabdus luminescens*. In one aspect, the second insect resistance gene encodes an insecticidal gene from *Bacillus thuringiensis*. Preferably, the second insect resistance gene encodes a Cry gene from the bacterium *Bacillus thuringiensis*, which Cry gene produces a toxin with a different mode of action or binding site in the insect gut to VIP for the control of different insect species. The Cry gene may, for example, be Cry1Ab.

The present invention further provides plant material derived from the COT202 event which possesses an additional trait such as herbicide resistance, nematode resistance or fungal resistance. In one embodiment, said additional trait is herbicide resistance. The herbicide resistance trait may be provided, for example, by a herbicide degradation enzyme, or a target-site specific resistant enzyme. In a further embodiment, said herbicide resistance trait provides resistance to a herbicide which comprises glyphosate acid or an agriculturally acceptable salt thereof. In a further embodiment still, said herbicide resistance trait is provided by a gene encoding EPSP synthase or a mutant thereof.

The present invention further provides a method of controlling insects comprising providing the COT202 event or plant material derived from the COT202 event at a locus where said insects feed. The invention yet further provides a method of controlling insects comprising providing the COT202 event or plant material derived from the COT202 event at a locus where said insects feed, and applying other agrochemicals to said plant material such as herbicides, fungicides and other insecticidal compounds including other insecticidal proteins. Examples of possible insecticidal compounds include insecticidal lectins, insecticidal protease inhibitors and insecticidal proteins derived from species of the *Bacillus thuringiensis, Xenorhabdus nematophilus*, or *Photorabdus luminescens*. Examples of possible chemicals include pyrethroids, carbamates, imidacloprid, organochlorines, and macromolecules such as spinosad, abamectin or emamectin.

According to yet a further aspect of the present invention, there is provided a method of detecting the COT202 event or plant material derived from the COT202 transgenic event comprising obtaining a sample for analysis; extracting DNA from the sample; providing a pair of primers designed to bind to a polynucleotide comprising at least 17 contiguous nucleotides of SEQ ID NO: 1 and/or SEQ ID NO: 2; amplifying the region which lies between the sites at which the primers bind; and detecting the presence of the amplification product. Suitable pairs of primers for use in this method of detection can be designed using parameters well known to those skilled in the art of molecular biology now that SEQ ID NOs 1 and 2 are made available. For example, one or both primers of the pair may be designed to be vector-specific, trait gene specific, promoter specific, and/or specific to the sequence of the junction between the inserted DNA and the genomic DNA. Preferably one of the primers is designed to be specific to the inserted sequence, and the other primer specific to the genomic DNA upstream or downstream of the insertion site. In one embodiment, the sequence of said primers is depicted as SEQ ID NO: 3 and SEQ ID NO: 4.

In an embodiment of the present invention, the region amplified by said method (the 'amplicon') is between 100 and 1000 base pairs in length. In a further embodiment the amplicon is between 100 and 400 base pairs in length. In a still further embodiment the amplicon is 181 base pairs in length. In a further embodiment the amplicon is produced using the above method in conjunction with the primers of the sequence of SEQ ID NO: 3 and SEQ ID NO: 4, and is 181 base pairs in length. These primers are specific for the COT202 event.

Alternative primers which may be used in combination to detect the COT202 event include SEQ ID NOs 13 and 14 which are specific for the COT202 event and produce an 86 bp amplicon, and SEQ ID NOs 5 and 6 which are specific for the VIP gene and produce a 556 bp amplicon.

There are many amplification methods that may be used in accordance with this aspect of the invention. The underlying principle, a known technique to those skilled in the art, is the polymerase chain reaction (PCR). The amplification product from a PCR reaction may be visualized by staining with ethidium bromide and excitation with UV light, typically after size separation using agarose gel electrophoresis.

An embodiment of the present invention employs variations of the PCR principle such as TaqMan™. This involves labelling at least one of the primers involved in the amplification process with a fluorescent dye. When unbound, the primer adopts a conformation such that no fluorescence can be detected. However, when the primer is bound to a piece of DNA, the conformation changes and fluorescence can be detected. In this way, the amplification process can be monitored in real-time, the intensity of fluorescence corresponding directly to the level of amplification. Suitable primers for use in TaqMan™ PCR are depicted as SEQ ID NOs 13 to 15. These may be used in conjunction with internal control primers such as those depicted as SEQ ID NOs 10 to 12. TaqMan™ analysis may be useful for example, for detecting the presence of the COT202 event in a background of wild type cotton, or for detecting the adventitious presence of COT202 in other germplasm. Further embodiments of the present invention include, but are not limited to, RACE PCR.

A further embodiment of the present invention involves the use of multiplex PCR for distinguishing between homozygous COT202 plant material and heterozygous COT202 plant material. This is known to those skilled in the art as zygosity testing, and involves the use of three PCR primers which bind to specific parts of the cotton genome and/or inserted DNA. The presence or absence of each of two amplification products of particular sizes indicates whether the test sample is heterozygous or homozygous for COT202. Suitable primers for use in such a zygosity test are depicted as SEQ ID NOs 16 to 18.

In another aspect of the invention there is provided a method of detecting plant material derived from the COT202 event comprising obtaining a sample for analysis; providing a probe designed to bind to the complement of a polynucleotide which comprises at least 17 contiguous nucleotides of SEQ ID NO: 1 and/or SEQ ID NO: 2 when said polynucleotide is single stranded; hybridizing said probe with the sample; and detecting whether the probe has hybridized. In one embodiment, said probe comprises the sequence of SEQ ID NO: 1 and/or SEQ ID NO: 2. In an embodiment of the present invention there is provided a method of detecting plant material derived from the COT202 event using a probe comprising SEQ ID NO: 7 or SEQ ID NO: 8. In one embodiment, said probe comprises SEQ ID NO: 7. In a further embodiment, said probe consists of SEQ ID NO: 7. In one embodiment, said probe comprises SEQ ID NO: 8. In a further embodiment, said probe consists of SEQ ID NO: 8. The probe may be, for example, a PCR product or restriction digestion fragment. In a further embodiment, the probe as described herein may be tagged with a fluorescent, radioactive, enzymatic or other suitable label to enable hybridization to be detected. The skilled man will know how to design suitable probes, now that he has the benefit of the present disclosure.

In a further embodiment of the present invention, there is provided a method of hybridizing a probe to the sample under stringent conditions and detecting whether the probe has hybridized. Stringent hybridization conditions are well known to the skilled man and comprise, for example: hybridization at a temperature of about 60° C. in a solution containing 6×SSC, 0.01% SDS and 0.25% skimmed milk powder, followed by rinsing at the same temperature in a solution containing 1×SSC and 0.1% SDS. More stringent hybridization conditions may comprise: hybridization at a temperature of about 65° C. in a solution containing 6×SSC, 0.01% SDS and 0.25% skimmed milk powder, followed by rinsing at the same temperature in a solution-containing 0.2×SSC and 0.1% SDS.

Suitable techniques for detecting plant material derived from the COT202 event based on the hybridization principle include, but are not limited to Southern Blots, Northern Blots and in-situ hybridization. The skilled man is familiar with techniques such as these. Typically, they involve incubating a probe with a sample, washing to remove unbound probe, and detecting whether the probe has hybridized. Said detection method is dependent on the type of tag attached to the probe—for example, a radioactively labelled probe can be detected by exposure to and development of x-ray film. Alternatively, an enzymatically labelled probe may be detected by conversion of a substrate to effect a colour change.

In a further aspect of the invention there is provided a method of detecting plant material derived from the COT202 event comprising obtaining a sample for analysis; providing an antibody or binding protein designed to bind to a VIP protein contained within a plant comprising at least 17 contiguous nucleotides from SEQ ID NO: 1 and/or SEQ ID NO: 2; incubating said antibody or binding protein with the sample; and detecting whether the antibody or binding protein has bound. In one embodiment of the present invention said VIP protein comprises the sequence of SEQ ID NO: 9.

Suitable methods of detecting plant material derived from the COT202 event based on said antibody binding include, but are not limited to Western Blots, Enzyme-Linked ImmunoSorbent Assays (ELISA) and SELDI mass spectrometry. The skilled man is familiar with these immunological techniques. Typical steps include incubating a sample with an antibody that binds to the VIP protein, washing to remove unbound antibody, and detecting whether the antibody has bound. Many such detection methods are based on enzymatic reactions—for example the antibody may be tagged with an enzyme such as horse radish peroxidase, and on application of a suitable substrate, a colour change detected. Suitable antibodies may be monoclonal or polyclonal.

In another aspect of the invention there is provided a method of detecting plant material derived from the COT202 event comprising obtaining a sample for analysis; making a protein extract of the sample; providing a test strip designed to detect the presence of a VIP protein present within the sample; incubating the test strip with the sample; and detecting whether VIP protein is present. In one embodiment of the present invention said VIP protein comprises the sequence of SEQ ID NO: 9.

An alternative antibody-based detection method for COT202 uses of dipsticks or test strips. Typical steps include incubating a test strip with a sample and observing the presence or absence of coloured bands on the test strip. The coloured bands are indicative of the presence of a protein in the sample. Such dipstick or test strip tests are protein specific, and may be used for rapid testing of samples in the field.

In a further aspect of the present invention there is provided a method of detecting plant material derived from the COT202 event comprising obtaining a sample for analysis; subjecting one or more insects of the species *Spodoptera frugiperda* (susceptible to VIP3A) to the sample; subjecting one or more insects of species *Ostrinia nubilalis* (not susceptible to VIP3A) to the sample as a control; detecting whether the sample has an insecticidal effect on insects from each species; and comparing the results with an authentic COT202 bioassay profile. The results are compared against an authentic COT202 bioassay profile that is produced using insects of the same condition (including insect age and culture conditions) which have been subjected to the same dose and type of COT202 plant material (including plant age, plant variety and tissue type) and where the insecticidal effect is detected the same length of time after subjecting the insects to the COT202 sample. Detection of an insecticidal effect may be, for example, an assessment of insect mortality, or of the growth stage of the insects. *Spodoptera frugiperda* is a positive control for COT202 as it is susceptible to a suitable dose of VIP3A, while *Ostrinia nubilalis* is a negative control for COT202 as it is not susceptible to a suitable dose of VIP3A. Alternative insect species that are either susceptible or not susceptible to VIP3A may be substituted in an assay as described above as appropriate, provided that the results are compared against an authentic profile generated using the same insect species.

In one embodiment of the invention, the method of detecting plant material derived from the COT202 event includes but is not limited to leaf-feeding bioassays in which a leaf or other suitable plant part from the COT202 event or any plant material derived from the COT202 event, is infested with one or more pest insects. Detection may be through assessment of damage to the leaf or plant part after set time periods, assessment of mortality or another insecticidal effect on the insects. Alternative plant parts which may be used for such bioassays include bolls and squares. Such bioassays may, for example, be carried out in the laboratory, field, or glasshouse, and may be subject to natural or artificial insect infestation.

In another aspect of the invention, there is provided a kit of parts comprising a means for detecting the presence in a sample of plant material derived from the COT202 event. Preferably, said kit of parts comprises a means for detecting the presence in a sample of a polynucleotide comprising at least 17 contiguous nucleotides from the sequence of SEQ ID NO: 1 and/or SEQ ID NO: 2, or a protein encoded by a polynucleotide as described above, or a VIP protein. In an embodiment of the present invention, said kit of parts may comprise DNA amplification-detection technology such as PCR or TaqMan™. In a further embodiment of the present invention, said kit of parts may comprise probe hybridization-detection technology such as Southern Blots, Northern Blots or in-situ Hybridization. In another embodiment of the present invention, said kit of parts may comprise antibody binding-detection technology such as Western Blots, ELISA's, SELDI mass spectrometry or test strips. In a further embodiment of the present invention, said kit of parts may comprise insect bioassay-detection technology such as leaf feeding bioassays or mortality bioassays. Each of these detection technologies may be used as described above. In a further embodiment of the present invention, said kit of parts may comprise any combination of the afore-mentioned detection technologies. In a still further embodiment, said kit of parts may comprise in the form of instructions one or more of the methods described above.

According to the present invention, there is provided the use of one or more of the polynucleotides of the invention as described above for detecting the COT202 event. In one embodiment, said polynucleotides may be used in a method for detecting the COT202 event as described above.

EXAMPLES

The invention will be further apparent from the following non-limiting examples in conjunction with the associated sequence listings as described below:

SEQ ID NO 1: Polynucleotide sequence which extends across the junction where the 5' end of the COT202 insert is inserted into the cotton genome in event COT202.

SEQ ID NO 2: Polynucleotide sequence which extends across the junction where the 3' end of the COT202 insert is inserted into the cotton genome in event COT202.

SEQ ID NOs 3-6: Polynucleotide sequences suitable for use as primers in the detection of the COT202 event.

SEQ ID NOs 7-8: Polynucleotide sequences suitable for use as probes in the detection of the COT202 event.

SEQ ID NO 9: Amino acid sequence of the VIP3A toxin protein.

SEQ ID NOs 10-15: Polynucleotide sequences suitable for use as TaqMan™ primers in the detection of the COT202 event.

SEQ ID NOs 16-18: Polynucleotide sequences suitable for use as primers in the detection of the COT202 event via zygosity testing.

Example 1

Cloning and Transformation 1.1 Vector Cloning

Standard gene cloning techniques of restriction digestion and ligation of fragments from in-house vectors were used to construct the transformation vector, pNOV103. The vector included a selectable marker cassette comprising a Ubiquitin (UBQ3) promoter, the UBQ3 intron, a gene sequence which encodes a protein conferring resistance to hygromycin, and a nos polyadenylation sequence. The vector also included the expression cassette of the target gene, which cassette comprised a Ubiquitin (UBQ3) promoter, the UBQ3 intron, a sequence encoding the VIP3A gene that had been codon optimised for expression in maize, and a nos polyadenylation sequence. The selectable marker cassette and VIP3A containing cassette were cloned between the left and right border sequences within different T-DNA regions of vector pNOV103. The vector also comprised a gene conferring resistance to an antibiotic, kanamycin, for prokaryotic selection.

The vector was transformed into *Agrobacterium tumefaciens* strain GV3101 using standard *Agrobacterium* transformation techniques, and transformed cells selected through their resistance to kanamycin.

1.2 Plant Transformation

The COT202 event was produced by *Agrobacterium*-mediated transformation of *Gossypium hirsutum* L. cv Coker 312.

Coker 312 seeds were sown in the glasshouse. Tender petioles were cut from 3 to 5 weeks old plants, and sterilized by immersion in 70% ethanol. The petioles were then immersed in a 5% Clorox+2 ml/L Tween 20 solution for 20 minutes. Petioles were washed 3 times in $ddH_2O$. The ends of petioles were cut off, and petioles transferred to petiole pre-culture medium (4.3 g(L MS salts, 200×B5 vitamins, 30 g/L glucose, 2.4 g/L phytogel, pH 7.0) and allowed to pre-culture in the light at 30° C. for 3 days.

2 ml cultures of *Agrobacterium* containing the pNOV103 construct were grown overnight in appropriate antibiotics and then diluted with liquid MMS1 medium (4.3 g/L MS salts, 200×B5 vitamins, 0.05 mg/L 2,4-D, 0.1 mg/L kinetin, 30 g/L glucose, pH 6.5) to an $OD_{660}$ of between 0.1 and 0.2.

The ends were cut off the petioles and placed in 3 to 5 ml of bacterial solution in a sterile petri dish. Once in the solution, the petioles were cut lengthwise and then cut into 2 cm sections. After the petiole explants had soaked in bacterial solution for 5 to 10 minutes, they were transferred to co-culture plates, and allowed to co-culture at 24° C. for 48 hours under low light intensity. Co-cultured explants were transferred to MMS1 medium (recipe as for MMS1 liquid medium, additionally with 2.4 g/L phytogel) containing 500 mg/L Cefotaxime and 10 mg/L Hygromycin, and incubated at 30° C. under a light cycle of 16 hours light and 8 hours dark. Explants were transferred to fresh medium after 2 weeks, and every 4 to 6 weeks thereafter until callus was formed.

Once calli were the size of a garden pea, they were removed from the explants and transferred to fresh MMS1 medium containing 500 mg/L Cefotaxime and 10 mg/L Hygromycin, and maintained in tissue culture by subculturing every 4 weeks as appropriate.

1.5 g callus tissue was broken up thoroughly and placed in a 50 ml Erlenmeyer flask containing 10 ml of liquid MMS2 medium (4.3 g/L MS salts, 200×B5 vitamins, 1.9 g/L KNO$_3$, 30 g/L glucose, pH 6.5). The suspended callus was shaken at 100 rpm in the light at 30° C. until small white slightly round cell clusters were visible. These clusters indicate that the tissue is embryogenic. The suspension culture cells were rinsed 3 times in MMS2 liquid medium, resuspended and plated onto solid MMS2 medium (recipe as per liquid MMS2 medium, additionally with 2.4 g/L phytogel). Once plated, excess liquid MMS2 medium was removed, and the plates incubated at 30° C. in the light. Plates were checked for somatic embryo development each week. Somatic embryos formed within 1 to 2 months. Somatic embryos were transferred to EG (embryoid germimation) medium (10×EG stock (consisting of 1×10 L pack of Musashige and Skoog Modified Basal Salt Mixture (Sigma), 19 g KNO3, 50 ml 200×B5 vitamins, water to 1 L), 1 g/L glutamine, 0.5 g/L asparagine, recipe), and sub-cultured to fresh EG medium every 3 to 4 weeks.

Once somatic embryos turned green and were larger than 2 cm, they were plated root down in EG medium. At all stages of regeneration, growing plantlets were prevented from reaching the lids or sides of their containers. Germinated embryos with 1 to 2 true leaves were transferred to EG medium in 175 ml Greiners. Strong plantlets with true leaves were transferred to sterile peat plugs expanded with dH$_2$O in 175 ml Greiners and transferred to a growth cabinet under conditions of 14 hours daylight at 30° C. and 10 hours darkness at 20° C. Thereafter, plantlets were transplanted into pots and grown in the glasshouse.

1.3 Identification and Selection of Transgenics

Putative transgenic plants were screened by PCR for the presence of the VIP3A gene. Positive events were identified and screened using insect bioassays for insecticidal activity against Fall Armyworm (*Spodoptera frugiperda*) (see Example 7). Insecticidal lines were characterized for copy number by TaqMan™ analysis (see Example 2). T1 seed from several events were observed in a field trial for insect resistance and agronomic quality. Two events, COT202 and COT203, were chosen based on having a single copy of the transgene, good protein expression as identified by ELISA (see Example 4), good insecticidal activity against Cotton Boll Worm (*Helicoverpa zea*) and field performance. The hygromycin selectable marker cassette was segregated away using conventional plant breeding to result in the COT202 event and the COT203 event.

1.4 Verification of Sequence of COT202

Genomic DNA was isolated from the COT202 event. This was used in the sequencing of the junctions of the DNA insertion site with the cotton genomic DNA in the COT202 event, using standard DNA sequencing techniques.

Example 2

COT202 Event Specific Detection via TaqMan™

2.1 DNA Extraction

DNA was extracted from leaf tissue using the Wizard™ Magnetic 96 DNA Plant System (Promega, #FF3760), according to the manufacturers instructions, with an additional step at the beginning of the protocol: following grinding of the leaf material, 0.9ml Cotton Extraction Buffer (0.2M Tris pH 8.0, 50mM EDTA, 0.25M NaCl, 0.1% v/v 2-mercaptoethanol, 2.5% w/v polyvinyl-pyrrolidone) was added to each well, the plant tissue resuspended and the plate centrifuged at 4,000 rpm (2755 g) for 10 minutes. After aspirating and discarding the supernatant, 300 ul Lysis Buffer A (Promega) was added and the manufacturers protocol was followed from this point. This procedure resulted in approximately 85 ul of purified genomic DNA at a concentration of approximately 10 ng/ul.

2.2 TaqMan™ TPCR Reactions

TaqMan™ PCR reactions were setup using a standard reaction mix comprising:

```
5 ul   2× Jumpstart Master Mix for Q-PCR (Sigma, #P2893),
       supplemented with 15 mM MgCl₂ and 200 nM Strata-ROX
0.2 ul 50× FAM primer/probe mix
0.2 ul 50× VIC primer/probe mix
1.6 ul Water.
```

50× primer/probe mixes comprised 45 ul of each primer at a concentration of 1mM, 50 ul of the probe at a concentration of 100 uM and 860 ul nuclease free water, and were stored in an amber tube at 4° C. Examples of suitable primer/probe sequence combinations which were used are:

| Primer Name | Primer Sequence 5'-3' | SEQ ID |
|---|---|---|
| GhCHI2b-F Forward | GGTCCCTGGATACGGTGTCA | SEQ ID NO: 10 |
| GhCHI2b-R Reverse | TTGAGGGTTGGATCCTTTGC | SEQ ID NO: 11 |
| GhGHI2bNEW-VIC Probe | CACCAACATCATCAATGGTGGCATCG (5' label = VIC, 3' label = TAMRA) | SEQ ID NO: 12 |
| COT202-F Forward | GGAATGTGGCGAATGGTGAT | SEQ ID NO: 13 |
| COT202-R Reverse | TGTCGTTTCCCGCCTTCA | SEQ ID NO: 14 |
| COT202-FAM Probe | CAAATTGCCCATTTCATTCATCCAAAAGC (5' label = FAM, 3' label = TAMRA) | SEQ ID NO: 15 |

7 ul of master mix was dispensed into each well of a 384-well TaqMan™ assay plate. 3 ul DNA template was added to the appropriate wells. 3 ul of copy control dilution series was added to specific wells as a control. The reactions were run in an ABI7900HT (Applied Biosystems) using the following cycling conditions:

| Step | Temperature | Time |
|------|-------------|------|
| 1 | 50° C. | 2 min |
| 2 | 95° C. | 10 min |
| 3 | 95° C. | 15 sec |
| 4 | 60° C. | 1 min |
| 5 | Goto step 3, repeat 40 times | |

Data was analyzed using SDS2.0 version A, software (Applied Biosystems).

Example 3

COT202 Detection via Multiplex PCR Zygosity Test 3.1 Genomic DNA Extraction

Genomic DNA from COT202 was extracted as described in Example 2.1.

3.2 Multiplex PCR

PCR primers were designed to bind to cotton genomic DNA sequence upstream of the site at which the COT202 cassette inserted (SEQ ID NO: 16); the cotton genomic DNA sequence downstream of the site at which the COT202 cassette inserted (SEQ ID NO: 17); and the COT202 cassette sequence itself (SEQ ID NO: 18). A 25 ul PCR reaction was set up for each sample to be tested as follows:

1× JumpState ReadyMix REDTaq PCR (Sigma P-1107)

0.5 uM primer 1 (SEQ ID NO: 16)

0.5 uM primer 2 (SEQ ID NO: 17)

0.5 uM primer 3 (SEQ ID NO: 18)

0.2% BSA 20 ng genomic DNA ddH2O to 25 ul

The PCR reactions were heated in a thermocycler at 94° C. for 5 minutes, followed by 30 cycles as follows: 94° C. for 30 seconds, 55° C. for 45 seconds, 72° C. for 1 minute. The reaction was completed by heating at 72° C. for 5 minutes.

3.3 Analysis

PCR reactions were run on an agarose gel, and DNA bands visualized under UV light after staining with ethidium bromide. The presence of 2 bands indicated that the sample was from a COT202 heterozygote plant; 1 band of 181 bp in size indicated that the sample was from a COT202 homozygote plant; and 1 band of approximately 400 bp in size indicated that the sample was from a homozygote wild type cotton plant.

3.4 COT202 Detection via Standard PCR

As an alternative to the multiplex PCR, the COT202 event can be detected in a simple PCR reaction using the primers depicted as SEQ ID NO: 3 and 4, SEQ ID NO: 13 and 14, or SEQ ID NO: 16 and 18. The composition of the PCR reaction mixture is the same as described in example 3.2 above. The PCR reactions are heated in a thermocycler at 94° C. for 5 minutes, followed by 30 cycles as follows: 94° C. for 30 seconds, 55° C. for 30 seconds, 72° C. for 20 seconds. The reaction is completed by heating at 72° C. for 5 minutes. A DNA fragment of 181 bp, 86 bp or 181 bp in size respectively indicates the presence of the COT202 event.

Example 4

COT202 Detection Via Southern Blot 4.1 DNA Extraction for Use in Southern Blotting Approximately 2 to 3 g fresh weight of young leaf tissue was ground in a chilled mortar and pestle to a fine powder and added to 15 ml of ice-cold Nuclei extraction buffer (0.35M glucose, 0.1M Tris-HCl pH 8, 50mM $Na_2EDTA$, 2% Polyvinyl-pyrrohdone-10, 0.1% ascorbic acid, 0.2% B-mercaptoethanol) in a labelled tube. The sample was incubated on ice for 15-20 minutes. The tube was mixed gently and centrifuged at 2700 g for 20 minutes at 4° C. The supernatant was discarded and 8 ml of nuclei lysis buffer (0.14M sorbitol, 0.22M Tris-Cl pH 8, 0.8M NaCl, 0.22M $Na_2EDTA$, 0.8% w/v CTAB, 1% Sarkosyl, 1% Polyvinyl-pyrrolidone-10, 0.1% ascorbic acid, 0.2% B-mercaptoethanol, 5 μg/ml proteinase K) was added. After mixing, the tubes were incubated at 65° C. for 30 minutes. 10 ml chloroform was added, and the tube mixed gently by inversion until an emulsion formed followed by centrifugation at 4600 rpm for 10 minutes at room temperature.

The aqueous layer was removed into a new tube containing 10 μl RNase A (10 mg sigma R4642), and the tube incubated for 30 minutes at 37° C. The chloroform and centrifugation steps were repeated once. The aqueous layer was removed into a new tube containing 10 ml propan-2-ol. After approximately 15 minutes incubation at room temperature, a gelatinous precipitate was observed in the middle of the tube. The tube was mixed gently to precipitate out the DNA. The DNA was spooled out using a sterile loop into a falcon tube containing 70% ethanol. The DNA was air-dried to remove the ethanol and resuspended in 200-400 μl TE.

4.2 Alternative Method for DNA Extraction 2-3 young cotton leaves (approximately 1 g fresh weight) are ground to a paste in a mortar and pestle at room temperature, with 2 ml of grinding buffer (100mM NaOAc pH 4.8, 50mM EDTA pH 8.0, 500mM NaCl, 2% PVP (10,000MW), 1.4% SDS) and a little sand. The ground tissue is transferred to a 15 ml falcon tube, and the remnants in the mortar rinsed with 1 ml of grinding buffer into the tube. The sample is incubated at 65° C. for 15 minutes, shaking occasionally. 4 ml 10M ammonium acetate is added, and the sample mixed well and incubated at 65° C. for 10 minutes to precipitate proteins. The samples are incubated at room temperature at 4600 rpm for 10 minutes. The aqueous phase is transferred to a fresh 15 ml tube.

0.6 volumes of cold isopropanol are added and the sample is incubated at room temperature for approximately 30 minutes. After mixing by slowly inverting the tube several times, the DNA is spooled out and dissolved in 500 ul TE. 10 ul of 10 mg/ml RNAse are added and incubated for 15 minutes at room temperature. Following extraction with 500 ul of phenol: chloroform: isoamyl alcohol (25:24:1), the sample is mixed gently and centrifuged at 13000 rpm for 5 min.

The supernatant is transferred to a fresh tube using a fine Pasteur pipette and re-extracted with chloroform: isoamyl alcohol (24:1) as above. The supernatant is transferred to fresh tubes, 1/10 volume 3M NaOAc (pH 4.8) added and mixed, and then one volume cold isopropanol is added. The sample may be incubated at room temperature for up to 30 minutes to precipitate the DNA. The DNA is spooled out and resuspended in 70% ethanol. The DNA is air-dried to remove the ethanol and resuspended in 200 ul water.

4.3 Restriction Enzyme Digests

The DNA was quantified using a spectrophotometer and running out on a gel. Suitable enzyme digests were prepared using 5 ug DNA per digest in a total volume of 40 ul. Digests included HindIII, XmaI, BamHI, NheI, and SacI, both alone and in combination. In particular, a HindIII and XmaI double digest was used to detect the intactness of the VIP3A gene; a NheI digest was used to detect VIP3A locus number. Digests were incubated for 6 hours at the appropriate temperature for each enzyme.

4.4 Gel Electrophoresis

Bromophenol blue loading dye was added to each sample from 4.2 above, and each sample loaded on a 0.8% TBE agarose gel. The gel was run at 50 volts overnight.

After running, the gel was washed in 0.25M HCl for 10 minutes to depurinate the DNA, incubated in denaturing solution (0.5M NaOH, 1.5M NaCl) with gentle agitation for 30 minutes, rinsed with distilled water and then incubated in neutralizing solution (0.5 M Tris, 1.5M NaCl) for 30 minutes.

A Southern Blot was prepared as follows: A glass plate was placed over a tray containing 20×SSC and a strip of 3M paper was placed onto the glass plate such that both ends dipped into the 20×SSC solution (to act as a wick). A piece of 3M paper the same size as the gel was placed on the wick, and the gel placed on this. Strips of nescofilm were laid around the edges of the gel to form a seal. A Hybond membrane was placed on top of the gel, followed by two further pieces of 3M paper. Throughout the assembly of the blot, care was taken to ensure that no air bubbles were trapped between the membrane, gel and 3M paper. A 5 cm-10 cm stack of absorbent paper towels was placed on top of the 3M paper and held in place with a weight.

The DNA was allowed to transfer to the Hybond membrane overnight. After transfer the Southern Blot stack was disassembled and the DNA was bound to the membrane via UV cross-linking.

4.5 Hybridization

A suitable DNA probe was prepared by PCR or restriction digest of binary plasmid. 25 ng probe DNA in 45 ul TE was boiled for 5 minutes, placed on ice for 5 minutes then transferred to a Rediprime II (Amersham Pharmacia Biotech, #RPN1633) tube. After addition of 5 ul P32-labelled dCTP to the Rediprime tube, the probe was incubated at 37° C. for 1 hour. The probe was purified by centrifugation through a microspin G-50 column (Amersham Pharmacia Biotech, #27-5330-01) according to the manufacturers instructions to remove unincorporated dNTPs. The activity of the probe was measured roughly by comparing the amount of radioactive component remaining in the column to the amount in the sample tube, with a ratio of at least 50:50 being acceptable. The Hybond membrane was pre-hybridized by wetting with 40 ml pre-warmed Rapid-Hyb buffer (Amersham-Pharmacia), at 65° C. for 30 minutes. The labelled probe was boiled for 5 minutes, and placed on ice for 5 minutes. An appropriate amount of probe (1 million counts per 1 ml pre-hybridization buffer) was added to the pre-hybridization buffer and hybridization occurred at 65° C. overnight. The following day, the hybridization buffer was discarded, and following a rinse with 50 ml 2×SSC/1% SDS solution the membrane washed in 150 ml 2×SSC/1% SDS solution at 65° C. for 30-45 minutes. This process was repeated twice with 0.1×SSC/1% SDS solution. The membrane was exposed to a phosphor screen or X-ray film to detect where the probe had bound.

Example 5

COT202 Detection Via ELISA

5.1 Protein Extraction

Cotton tissue for analysis was harvested and frozen at −70° C. Fresh tissue was ground to a fine powder and weighed into a labelled polypropylene tube. Extraction buffer (100mM Tris, 100mM Sodium Borate, 5mM MgCl, 0.05% Tween 20, 0.2% Sodium Ascorbate, Water, pH 7.8, 1mM AEBSF, 0.001mM Leupeptin) was added to the sample in a ratio of 2:1 (volume extraction buffer: sample fresh weight) for fresh tissue or 30:1 (volume extraction buffer: sample dry weight) for lyophilised tissue. The sample was vortexed and homogenized using a Brinkman PT 10/35 Polytron equipped with a PTA 10TS foam-reducing generator, until the mixture became liquefied. Extracts were centrifuged at 10,000×g for 15 minutes. The protein extract supernatant was stored at 2-8° C.

5.2 ELISA Protocol

The ELISA procedure used standard techniques as follows. A 96-well plate was soaked in ethanol for 2 hours, and air-dried. The plate was coated with 50 ul goat anti-VIP3A antibody per well and incubated overnight at 2-8° C. After washing three times with 1× ELISA wash solution (100mM Tris, 0.5% Tween-20, 75mM NaCl, pH 8.5), the plate was dried briefly by tapping upside down on a paper towel. 150 ul blocking solution (10mM $NaPO_4$, 140mM NaCl, 1% BSA, 0.02% Sodium Azide, titrated to pH 7.4 with monobasic NaPi and dibasic NaPi) was added to each well followed by incubation at room temperature for 45 minutes. The plate was washed 3 times as described above.

VIP3A standards and protein extract samples were applied to appropriate wells of the plate in triplicate, 50 ul total volume per well. The plate was incubated at 2-8° C. for 1 hour 30 minutes, followed by room temperature for a further 30 minutes. The plate was washed three times with ELISA wash solution, and then incubated at 35-39° C. for 1 hour with 50 ul rabbit anti-VIP3A antibody per well. The plate was washed three times with ELISA wash solution, and incubated at room temperature for 30 minutes with 50 ul donkey anti-rabbit alkaline phosphatase per well. Following a further three washes with ELISA wash solution, 5 ul phosphatase substrate solution was added per well and the plate incubated for 30 minutes at room temperature. The reaction was stopped by addition of 50 ul 3M NaOH per well. The absorbance of the solution in each well was measured at 405 nm using a Ceres 900C multiwell plate reader and the results analyzed using KC3 Curve fitting software (Bio-Tek Instruments Inc.). The concentration of VIP3A in the samples was calculated by reference to the VIP3A protein standards.

Example 6

COT202 Detection Via DipStick

6.1 Protein Extraction

A piece of leaf tissue approximately 2 $cm^2$ was placed in a tube containing extraction buffer. A plastic stirrer was used to extract protein from the tissue, by cutting into and mascerating the tissue.

6.2 Dipstick Test

A test strip was placed into the tube and incubated for 5 to 10 minutes for the result to develop. The test strip comprised a first band at which anti-VIP3A antibody was bound, and a second band at which a control antibody was bound. After incubation, a double red line in the result window of the test strip indicated that VIP3A was present. The lower line indicated the presence of VIP3A protein while the upper line was a control indicating that. the assay was working correctly.

Example 7

COT202 Detection Via Insect Bioassay 7.1 Leaf Biosassays

Leaf assays were performed on Fall Army Worm (*Spodoptera fugiperda*), Cotton Boll Worm (*Helicoverpa zea*) and Tobacco Budworm (*Heliothis virescens*) as follows: Pads were soaked with 300 ul to 500 ul distilled water and placed into Gelman dishes. Leaf pieces measuring between approximately 0.5 square inches and 0.75 square inches were excised from cotton plants 8 to 12 inches in height, and placed on the pads. Between 8 and 10 insect larvae were placed in each dish and a lid fitted. The dishes were incubated at 28° C. On the third and sixth days after infestation, damage to the leaf in each dish was scored and compared with the control plants.

7.2 Boll Bioassays

Four absorbent pads were saturated with water and placed inside a large plastic cup. Three extra thick glass filters, each soaked with 100 ul distilled water, were placed in a smaller plastic cup, which was then seated inside the larger cup. A 1.25 inch long boll was excised, immersed in 10 mg/ml to 20 mg/ml Nystatin and placed on the filters in the small cup. 50 insect larvae were placed on the square or boll and a lid attached to the larger cup. The squares or bolls were re-infested with 50 more larvae after 7 days.

The experiment was incubated at room temperature for approximately 3 weeks. The bolls were then cut open to determine damage. Damage to the boll was compared to the control samples.

7.3 Lyophilised Leaf Bioassays

Bioassays using freeze-dried leaf tissue were performed on *Heliothis virescens* as follows:

Terminal leaves were snap-frozen on dry-ice at time of picking and lyophilised overnight. The freeze dried tissue was ground in a mortar and pestle to a fine powder and resuspended in 0.2% agar solution to make an 8% (0.08 g/ml) suspension of leaf powder. The suspension was overlaid on top of artificial insect diet in 96-well plates and left to dry. A single neonate insect larva was introduced into each well and the plates sealed. The plates were incubated at 28° C. On the sixth day after infestation, larval mortality was scored and compared with control samples.

Example 8

COT202 Field Trials 8.1 Field Trial Design

The efficacy of the COT202 event against *Heliothis virescens* (Tobacco Bud Worm) and *Helicoverpa zea* (Cotton Boll Worm) was tested by conducting field trials at three locations in the US, namely Leland (MS), Quitman (GA) and Beasley (TX). Trials in each location were set up using a randomized complete block design, with four entry plots comprising four rows of 40 feet in length and four repetitions per trial. Seed was planted to obtain a plant stand of approximately 3 plants per foot of row length. Each field trial included non transgenic Coker 312 plants for control purposes, and two other transgenic events designated event A and event B for comparison purposes.

8.2 Field Trial Assessment

An assessment of the natural insect populations was made at each trial location at the first white flower stage, approximately 80 days after planting. Where insect pressure was below the US economic threshold of 10% damage, artificial infestation of Cotton Boll Worm and Tobacco Bud Worm was made. The artificial infestation method was designed to obtain a rate of 10 eggs per foot per insect species. Assessment of damage to cotton squares and bolls was made by visual inspection of 50 fruiting forms per plot at 5-7 days after artificial infestation. When relying on a natural infestation, damage ratings were made when the non transgenic Coker 312 control plants showed fruiting form damage above the economic threshold level of 10% in all control plots.

8.3 Field Trial Results

The results presented below show percentage damage to cotton squares and bolls at each field trial location, for each plant category. The data below represents an average of 200 fruiting forms (squares or bolls) per event per trial.

| Location: Leland, MS | | |
| --- | --- | --- |
| | Square Damage | Boll damage |
| Control | 77 | No data |
| COT202 event | 6.6 | No data |
| Event A | 3.6 | No data |
| Event B | 29.6 | No data |

| Location: Quitman, GA | | |
| --- | --- | --- |
| | Square Damage | Boll Damage |
| Control | 80 | 52 |
| COT202 event | 2 | 0 |
| Event A | 1.5 | 0 |
| Event B | 24.5 | 2 |

| Location: Beasley, TX, USA | | |
| --- | --- | --- |
| | Square Damage | Boll Damage |
| Control | 24.4 | 13.2 |
| COT202 event | 4 | 2 |
| Event A | 2 | 1.2 |
| Event C | 5.2 | 3.2 |

What is claimed is:

1. An isolated polynucleotide comprising the sequence of SEQ ID NO: 1 or SEQ ID NO: 2.

2. The isolated polynucleotide according to claim 1 comprising the sequence of SEQ ID NO: 8.

* * * * *